United States Patent [19]
Welles

[11] Patent Number: 5,643,173
[45] Date of Patent: Jul. 1, 1997

[54] METHOD AND APPARATUS FOR STRESS RELIEF

[76] Inventor: William F. Welles, 8343 Foothill Blvd., Pine Valley, Calif. 91962

[21] Appl. No.: 522,626

[22] Filed: Sep. 1, 1995

[51] Int. Cl.$^6$ ................................................ A61M 21/00
[52] U.S. Cl. .................................. 600/26; 607/45; 607/88
[58] Field of Search .......................... 128/734–5; 607/88, 607/93, 45, 46, 89; 600/26–28

[56] References Cited

U.S. PATENT DOCUMENTS

| | | | |
|---|---|---|---|
| 3,255,753 | 6/1966 | Wing | 600/26 |
| 3,835,833 | 9/1974 | Limoge | 600/26 |
| 4,014,323 | 3/1977 | Gilmer et al. | 128/734 |
| 4,408,617 | 10/1983 | Auguste | 128/735 |
| 4,535,784 | 8/1985 | Rohlicek et al. | 128/735 |
| 4,848,357 | 7/1989 | Wong et al. | 128/735 |
| 5,064,410 | 11/1991 | Frenkel et al. | 600/27 |
| 5,149,317 | 9/1992 | Robinson | 600/27 |
| 5,242,376 | 9/1993 | Shealy et al. | 600/27 |

FOREIGN PATENT DOCUMENTS

| | | | |
|---|---|---|---|
| 4009644 | 10/1991 | Germany | 128/735 |
| 1648471 | 5/1991 | U.S.S.R. | 128/735 |

Primary Examiner—Lee S. Cohen
Assistant Examiner—Bryan K. Yarnell
Attorney, Agent, or Firm—Charles C. Logan, II

[57] ABSTRACT

A stress relief apparatus having a square wave generator that is powered by a 9 volt d.c. battery. It has two separate closed circuits for transmitting an electrical square wave from the square wave generator. Each of these circuits have a light emitting diode that radiates a light in the 400–800 nanometer range. The structure for supporting the respective LED's would be a predetermined length of flex tubing having sufficient rigidity so that it can be bent to direct the light at preselected acupuncture points on either the triple warmer, small intestine or large intestine meridians. A first human body ground member is electrically connected to the square wave generator and a second human body ground member is connected to a ground. In one embodiment the human body ground members are a pair of metal cylinders one of which is gripped in each hand of the user. When the respective human body ground members are in contact with the human body, the square wave electrical signal will pass through the person's body between the respective human body ground members. A finger loop strap is used to support the flex tubing on the user's fingers. In a second embodiment the human ground member is the temple member of an eyeglass frame.

8 Claims, 2 Drawing Sheets

METHOD AND APPARATUS FOR STRESS RELIEF

BACKGROUND OF THE INVENTION

The invention relates to a method and apparatus for providing stress relief for humans. In industrial nations, the pressure of one's job, the requirement for sufficient money to support one's self and one's family and the desire for material wealth has caused many people to have an increased stress level. Smoking and drinking alcohol and other vices tend to further increase the stress level. Increased stress levels can be harmful to a person's health and can result in heart attacks, strokes and a host of other ailments. Some ways to reduce stress are by exercising and meditation.

Traditional American medicine has recently been supplemented with alternative types of treatments. One of these treatments is acupuncture, which is a traditional method of treating people from the Far East for thousands of years. Books about acupuncture describe numerous meridians that pass through the human body. Along the meridians are points that can be stimulated to promote healthful results.

Three of the meridians that travel along the arms of a person to their head are the triple warmer (TW), the small intestine (S.I.) and the large intestine meridians. Each of these meridians has a beginning point (BP) and an end point (EP). These points are also called sing points or acubane points. The reason the triple warmer meridian, the small intestine meridian and the large meridian have special neurological significance is they all begin in the hands and end in the head. The fact that they end in the head means they have input into the brain or neurology. Any point on these meridians can be used to positive advantage, especially if directed up the head, but for convenience the following points are most important for each meridian.

TW1 and TW23 are the respective beginning and end points on the triple warmer meridian. TW1 (also known as GUANCHONG) is located on the ulnar side of the ring finger, 0.1 cun posterior to the corner of the fingernail. When this acupuncture point is actuated, headaches and hysteria and other symptoms can be alleviated. TW3 (also known as ZHONGZHU) is on the dorsum of the hand between the forth and fifth metacarpal bones. Activation of this point often helps to alleviate headaches. TW23 ends at the end of the eyebrow.

Small intestine point 1 (SI1) is located at the ulnar side of the small finger, about 0.1 cun posterior to the corner of the fingernail. Activation of this point helps to alleviate headaches and other symptoms. The small intestine point 3 (SI3) is located at the end of the transverse crease proximal to the 5th metacarpi-phalangeal joint when the hand is half clinched. Activation of this point helps to alleviate stiffness or rigidity of the neck and also headaches. SI19 ends in front of the ear.

The large intestine point 1 (LI1) (also known as SHANGYANG) is located on the radial side of the index finger, 0.1 inch posterior to the fingernail. The large intestine 4 (LI4), (also known as the HEGU), is located on the middle of the second metacarpal bone, on the radial aspect. Actuation of this point alleviates headaches and other symptoms. LI20 ends lateral to the base of the nose.

SUMMARY OF THE INVENTION

The novel invention transmits square wave patterns into the human body through preselected acupuncture points and also through preselected parts of the body. The effect of these square wave patterns reduces stress in the individual being treated.

The stress relief apparatus has a square wave generator that is powered by a nine volt d.c. battery. Two separate closed circuits for transmitting an electrical square wave from the square wave generator are detachably secured to the square wave generator. Each of these circuits has a light emitting diode (LED) that radiates a light in the 400-800 nanometer range. The structure for supporting the respective LED's would be a predetermined length of flex tubing having sufficient rigidity so that it can be bent to direct the red light at preselected acupuncture points on either the triple warmer, small intestine, or large intestine meridians. It is also secured to the finger points via a Velcro strap. A first ground wire has its one end connected to a first output jack on the square wave generator housing and its other end is connected to a first human ground member. A second ground wire has its one end connected to a second output jack and its other end is connected to a second human ground member. The second ground wire has an electrical square wave transmitted through it. The respective first and second human ground members are placed in contact with a human body, the human body completes the electrical circuit between the respective human ground members and the electrical square wave is transmitted through the person's body.

In a first embodiment of the stress relief apparatus, the human body ground members are elongated electrically conductive rods that would be held in a person's hands to complete the electrical circuit for one of the square wave that is directed into the human body.

In a second embodiment of the stress relief apparatus, the ground members would be electrically conductive temple members of an eyeglass frame.

The combination of the square wave pattern that passes through a person's body and the square wave patterns that stimulate the acupuncture points, especially the beginning points of a meridian, seem to resonate into the person's mind to allow a state of ease and relaxation to come over the body. In this relaxed state of the mind while hooked up to the TW meridian, statements such as those below can be readily received in the mind: (1) I let go of all anxiety worry and fear and take in peace, rest and calm., (2) I want to be 100 percent healthy on all levels, (3) it is alright if I am 100 percent healthy, (4) it is safe to be 100 percent healthy on all levels, (5) I deserve to be 100 percent healthy on all levels, (6) It is okay to be 100 percent healthy on all levels, etc.

By repeating these statements, while hooked up to the combination of square wave pattern input and acupuncture point stimulation, these statements quickly become congruous with the belief structure of the individual. Statements 2-6 above fall into a category of statements of incongruence with health that are called reversals. Reversals are negative reversed beliefs we hold onto to the detriment of our mental and physical health.

The symptoms of headaches, irritability, blurring vision and insanity associated with the aforementioned acupuncture meridians are definitely mental symptoms which is why stimulating these acupuncture points in combination with square wave patterns seems to work most effectual for clearing stress and negative mental beliefs.

DESCRIPTION OF THE PREFERRED EMBODIMENT

Figure 1:
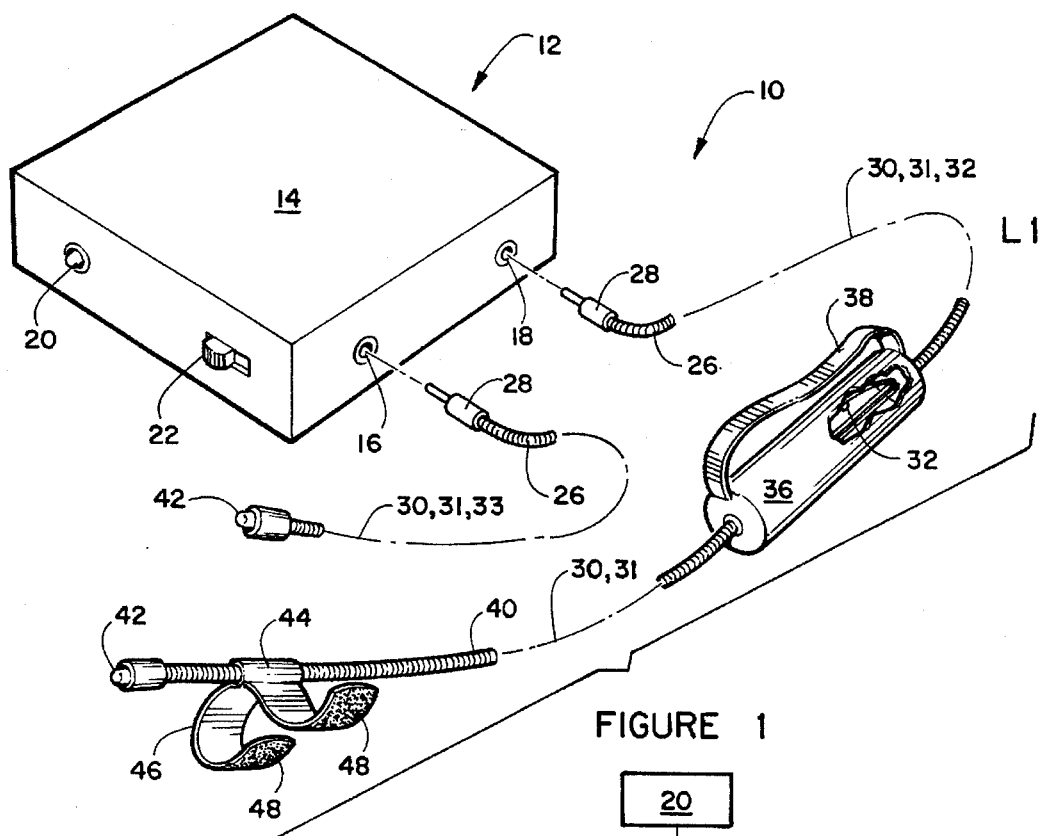
FIG. 1 is an exploded front perspective view of the novel stress relief apparatus.

The novel stress relief apparatus will now be described by referring to FIGS. 1–5 of the drawings. The stress relief apparatus is generally designated numeral 10.

Stress relief apparatus 10 has a square wave generator assembly 12 having a housing 14 with output jacks 16 and 18. An LED 20 is illuminated when switch 22 is actuated.

A pair of three electrical wire conductors 26 each have a male terminal 28 on their one end that is detachably inserted into the respective output jacks 16 and 18. The three conductor wires each have a length L1 that is in the range of 24 to 46 inches. Electrical wires 30,31 and 32 pass through one of these wire conductors with wire 32 being grounded on metal cylinder 36. Electrical wires 30,31 and 33 pass through the other wire conductor with wire 33 being grounded on metal cylinder 36. Wire 33 is connected to PC board 52 and it has a square wave electrical signal transmitted through it to metal cylinder 36. When a person is holding both of the metal cylinders 36 their body will complete the electrical circuit between them and the square wave electrical signal will be transmitted through their body.

Figure 2:
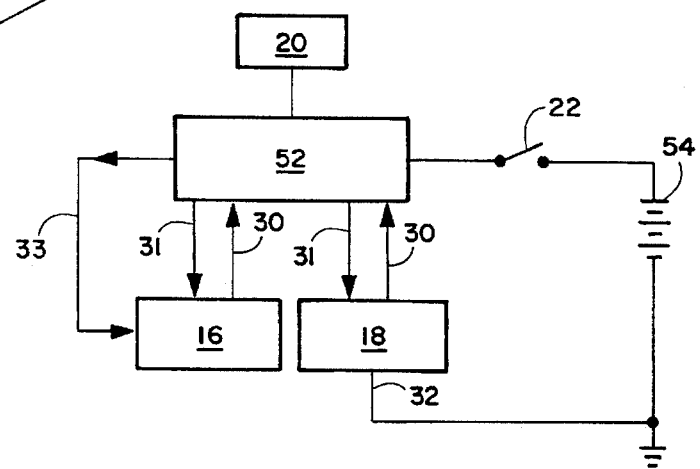
FIG. 2 is a schematic electrical diagram of the square wave generator assembly circuit.

Each metal cylinder 36 has an elastic strap 38 for holding it on the user's hand. Electrical wires 30 and 31 pass through metal cylinder 36 and also through flex tubing 40 and are connected to a red light emitting LED (600–680) 42 at its front end. The flex tubing 40 passes through tubular sleeve 44 on finger loop strap 46. Hook and loop fastening material 48 on finger loop strap allows it to be adjusted to different sized fingers. FIG. 2 illustrates a schematic diagram of the electrical circuit of square wave generator assembly 12. It has a PC board 52 having a square wave generator circuit mounted thereon that is powered by a 9 volt d.c. battery 54. This square wave pattern can be varied from a frequency range of 100 HZ to 200 KHZ and still be effective.

Figure 3:
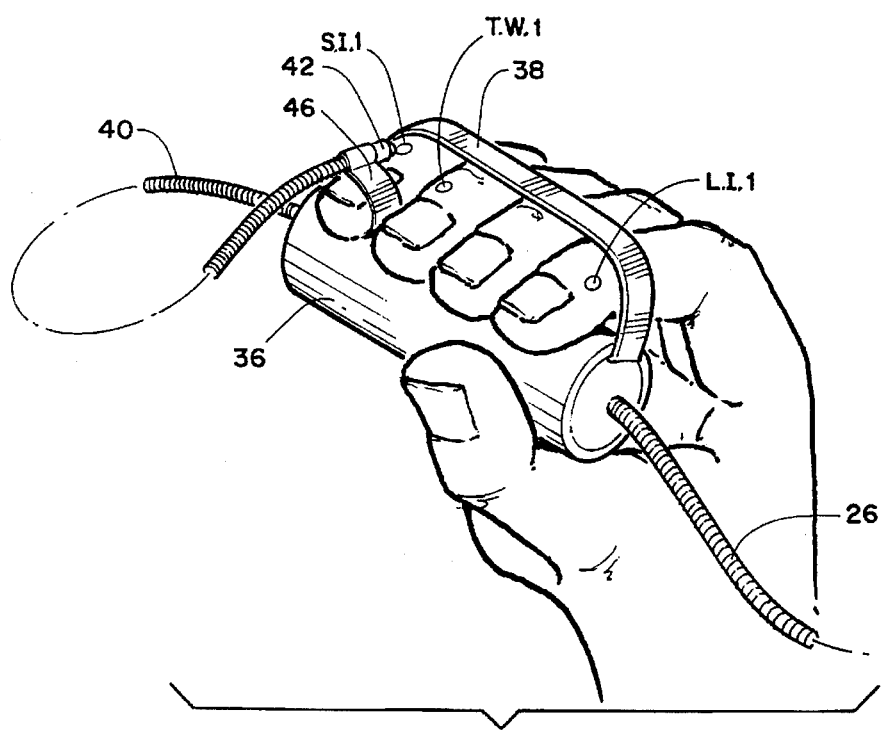
FIG. 3 is a front perspective view showing the manner in which the metal cylinder ground is supported in the users hand and how the flex tubing is supported on the user's fingers.

In FIG. 3, finger loop strap 46 is secured on the little finger of the wearer. The output of the LED 42 is directed at the small intestines 1 acupuncture point (SI1). Also shown in FIG. 3 is the large intestine acupuncture point 1 (LI1) and the triple warmer acupuncture point 1 (TW1).

Figure 4:
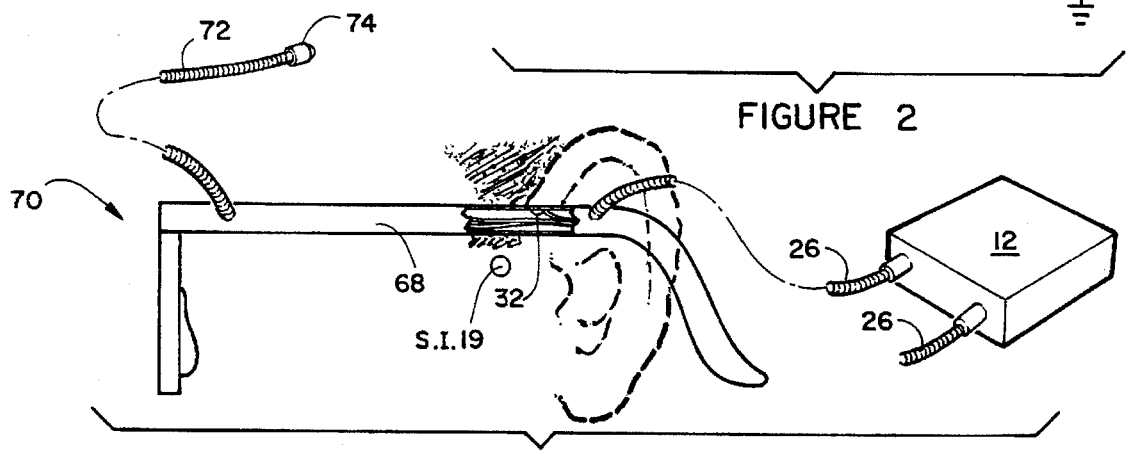
FIG. 4 is a side elevation view showing an alternative embodiment incorporated into the temples of an eyeglasses frame.
Figure 5:
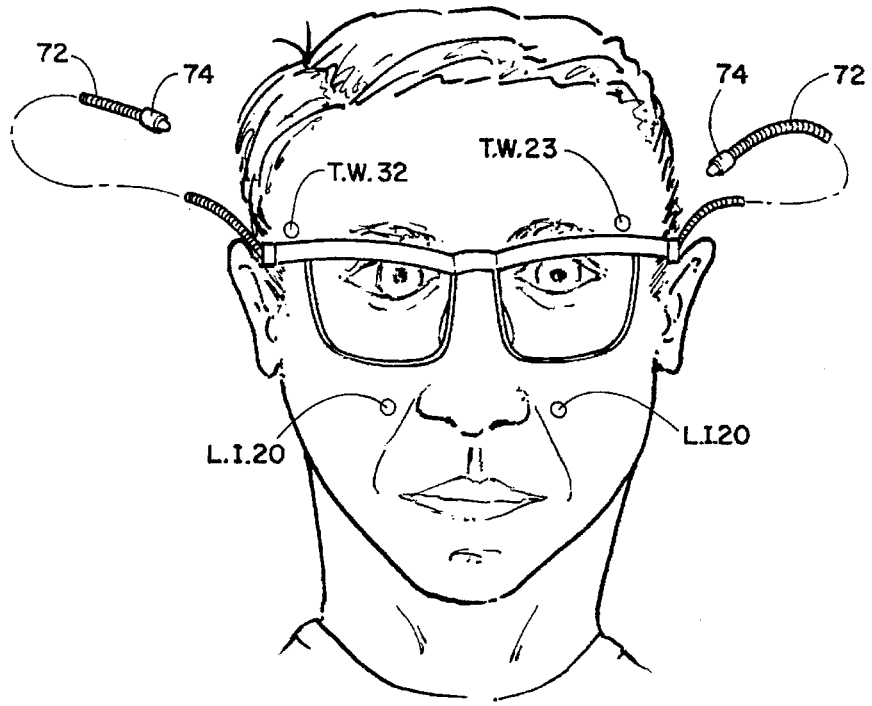
FIG. 5 is a front elevation view showing the eyeglasses frame embodiment worn by the user.

An alternative embodiment of the stress relief apparatus is illustrated in FIGS. 4 and 5. The same square wave generator assembly 12 is used along with the three strand electrical wire conductors 26. The major difference being that the temples 68 of eyeglasses frame 70 are used as the metal cylinder grounding member. Electrical wires 30,31 and 32 pass through one of the wire conductors 26 with wire 32 being grounded on metal temple 68. Electrical wires 30,31 and 33 pass through the other wire conductor 26 with wire 33 being grounded on the other metal temple 68. Wire 33 is connected to PC board 52 and it has a square wave electrical signal transmitted through it to metal temple 68. When a person is wearing eyeglasses frame 70 their body will complete the electrical circuit between temples 68 and the square wave electrical signal will be transmitted through their body. An LED 74 is connected at the front end of flex tubing 72 to the respective electrical wires 30 and 31. Temple 68 is made of metal material. Ground wires 32 and 33 are grounded on the respective temples 68.

When in use, the LED is directed at the triple warmer acupuncture point 23 (TW 23), the large intestine 20 (LI 20), or the small intestine acupuncture point 19 (SI 19).

What is claimed is:

1. Stress relief apparatus comprising:

a square wave generator assembly having means for emitting an electrical square wave pattern in the 100 HZ–200 KHZ range;

a source of electrical power connected to said square wave generator assembly;

a first light emitting diode (LED);

a first closed circuit for transmitting an electrical current from said square wave generator assembly to said first LED; said first closed circuit having a preselected length L1;

a first human body ground member and means for transmitting an electrical square wave to said first human body ground member from said square wave generator assembly;

a second light emitting diode (LED);

a second closed circuit for transmitting an electrical current from said square wave generator assembly to said second LED, said second closed circuit having a preselected length L1; and a second human body ground member and means electrically connecting it to ground in said square wave generator assembly.

2. A stress relief apparatus as recited in claim 1 wherein said source of electrical power is a battery.

3. A stress relief apparatus as recited in claim 2 wherein said battery is a 9 volt D.C. battery.

4. A stress relief apparatus as recited in claim 1 wherein said first and second LED, only emit light in the 400–800 nanometer range.

5. A stress relief apparatus as recited in claim 4 wherein said first and second LED's are unidirectional lights.

6. Stress relief apparatus comprising:

a square wave generator assembly having means for emitting an electrical square wave pattern;

a source of electrical power connected to said square wave generator assembly;

a first light emitting diode (LED);

a first closed circuit for transmitting an electrical current from said square wave generator assembly to said first LED; said first closed circuit having a preselected length L1;

a first human body ground member and means for transmitting an electrical square wave to said first human body ground member from said square wave generator assembly;

a second light emitting diode (LED);

a second closed circuit for transmitting an electrical current from said square wave generator assembly to said second LED, said second closed circuit having a preselected length L1;

a second human body ground member and means electrically connecting it to ground in said square wave generator assembly; and said first and second human body ground members are elongated electrically conductive rods to be held in a person's hands.

7. Stress relief apparatus comprising:

a square wave generator assembly having means for emitting an electrical square wave pattern;

a source of electrical power connected to said square wave generator assembly;

a first light emitting diode (LED);

a first closed circuit for transmitting an electrical current from said square wave generator assembly to said first LED; said first closed circuit having a preselected length L1;

a first human body ground member and means for transmitting an electrical square wave to said first human body ground member from said square wave generator assembly;

a second light emitting diode (LED);

a second closed circuit for transmitting an electrical current from said square wave generator assembly to said second LED, said second closed circuit having a preselected length L1;

a second human body ground member and means electrically connecting it to ground in said square wave generator assembly; and said first and second human body ground members are elongated temple members that form part of an eyeglass frame which when worn allows the temple members to contact the opposite sides of a person's head.

8. A method for reducing the stress level of a human being comprising the steps of:

a) connecting a square wave generator assembly to a first closed circuit for transmitting an electrical current to a first LED that only emits light in the 400–800 nanometer range;

b) connecting the same square wave generator assembly to a second LED that only emits light in the 400–800 nanometer range;

c) connecting a square wave generator in the same square wave generator assembly to a first human body ground member; said square wave generator emits a square wave pattern in the 100 hz–200 khz range;

d) connecting a second human body ground member to ground in said square wave generator assembly;

e) directing said first LED and said second LED at preselected acupuncture points on selected meridians of the person's body;

f) turning on the power of the square wave generator assembly to send electrical current to the first and second LED's causing them to emit light at the preselected acupuncture points of the person to reduce their stress level; square wave electrical signals are also directed concurrently from said square wave generator assembly to said first human body ground member and then through the person's body to the second body ground member to form a closed electrical circuit.

* * * * *